US010625088B1

(12) United States Patent
Chapman et al.

(10) Patent No.: US 10,625,088 B1
(45) Date of Patent: Apr. 21, 2020

(54) SYSTEMS AND METHODS FOR DOUBLE SEQUENTIAL DEFIBRILLATION

(71) Applicant: Physio-Control, Inc., Redmond, WA (US)

(72) Inventors: Fred W. Chapman, Newcastle, WA (US); Robert G. Walker, Seattle, WA (US); Mitchell A. Smith, Sammamish, WA (US); Blaine Krusor, Seattle, WA (US); William E. Crone, Fall City, WA (US); David J. Linville, Woodinville, WA (US); Steven Heightman, Redmond, WA (US); Tyson G. Taylor, Bothell, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 168 days.

(21) Appl. No.: 15/835,309

(22) Filed: Dec. 7, 2017

Related U.S. Application Data

(60) Provisional application No. 62/431,408, filed on Dec. 7, 2016.

(51) Int. Cl.
*A61N 1/39* (2006.01)

(52) U.S. Cl.
CPC ......... *A61N 1/3987* (2013.01); *A61N 1/3918* (2013.01); *A61N 1/39044* (2017.08); *A61N 1/3906* (2013.01); *A61N 1/3925* (2013.01); *A61N 1/3993* (2013.01)

(58) Field of Classification Search
CPC .. A61N 1/3906; A61N 1/3993; A61N 1/3987; A61N 1/3918; A61N 1/39044; A61N 1/3925

USPC .......................................................... 607/5
See application file for complete search history.

(56) References Cited

U.S. PATENT DOCUMENTS

| 8,965,501 B2 | 2/2015 | Sullivan |
| 2014/0046393 A1* | 2/2014 | Sullivan ............... A61N 1/3925 607/7 |

OTHER PUBLICATIONS

U.S. Appl. No. 62/410,283, filed Oct. 19, 2016, entitled "Precision timing of controlled dual-sequential defibrilation".
U.S. Appl. No. 62/410,290, filed Oct. 19, 2016, entitled "Methods for controlled double-sequential defibrillation".

* cited by examiner

*Primary Examiner* — Brian T Gedeon
*Assistant Examiner* — Philip C Edwards
(74) *Attorney, Agent, or Firm* — Lane Powell PC

(57) ABSTRACT

A defibrillation device for administering an electrotherapy, such as a dual-sequential defibrillation (DSD) electrotherapy. The defibrillation device can include a defibrillation therapy module, a physiological parameter module and a control module. The defibrillation therapy module can output one or more energies and the physiological parameter module can receive one or more physiological parameters, including electrocardiogram (ECG) data. The control module can analyze the physiological parameters to determine an indication for the administration of an electrotherapy and can determine a DSD electrotherapy. The DSD electrotherapy can be based at least in part on the physiological parameters, the indication for the administration of an electrotherapy or a review of the ECG data.

27 Claims, 5 Drawing Sheets

EXAMPLE ELECTRODE ARRANGEMENT

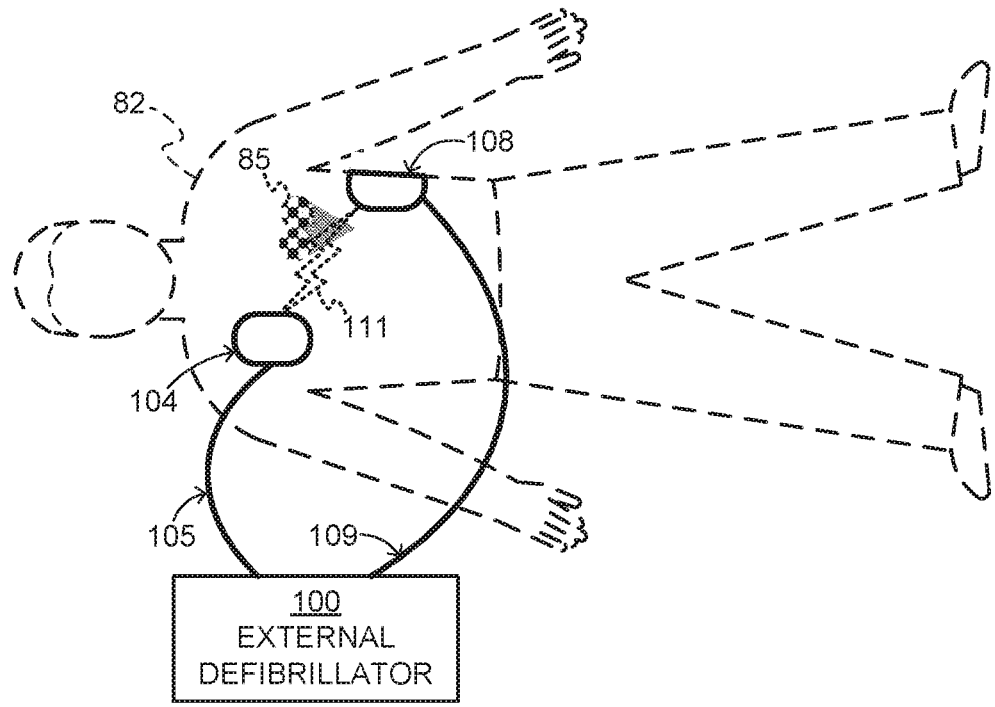
FIG. 1  *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *TWO MAIN TYPES OF EXTERNAL DEFIBRILLATORS*

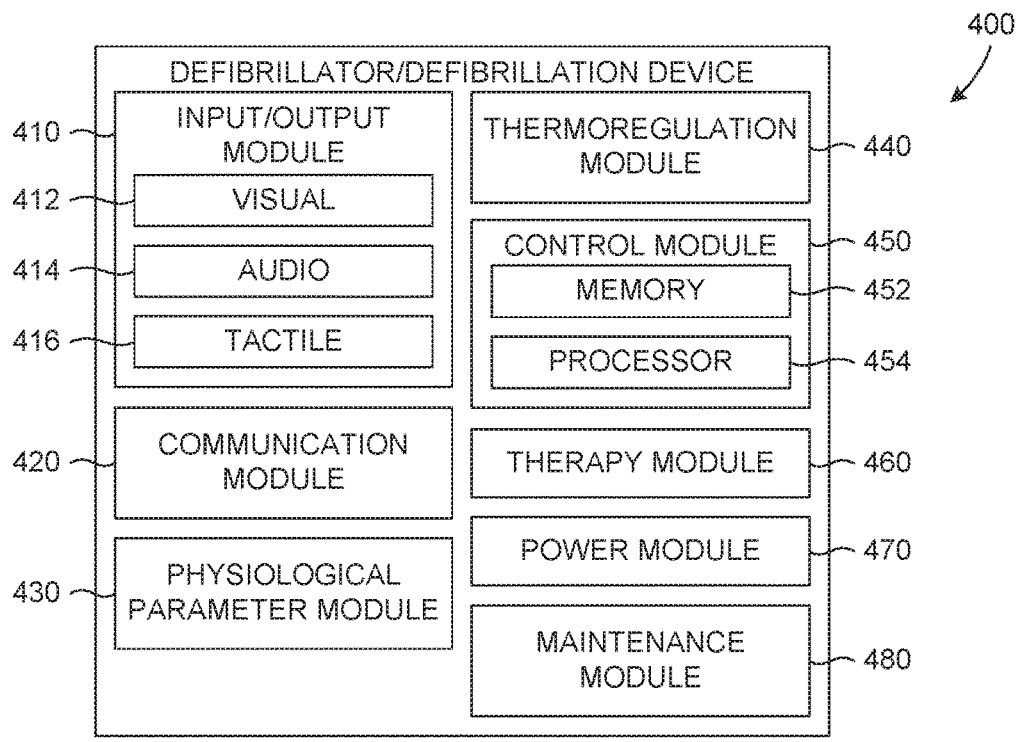
FIG. 4  *EXAMPLE DEFIBRILLATION DEVICE*
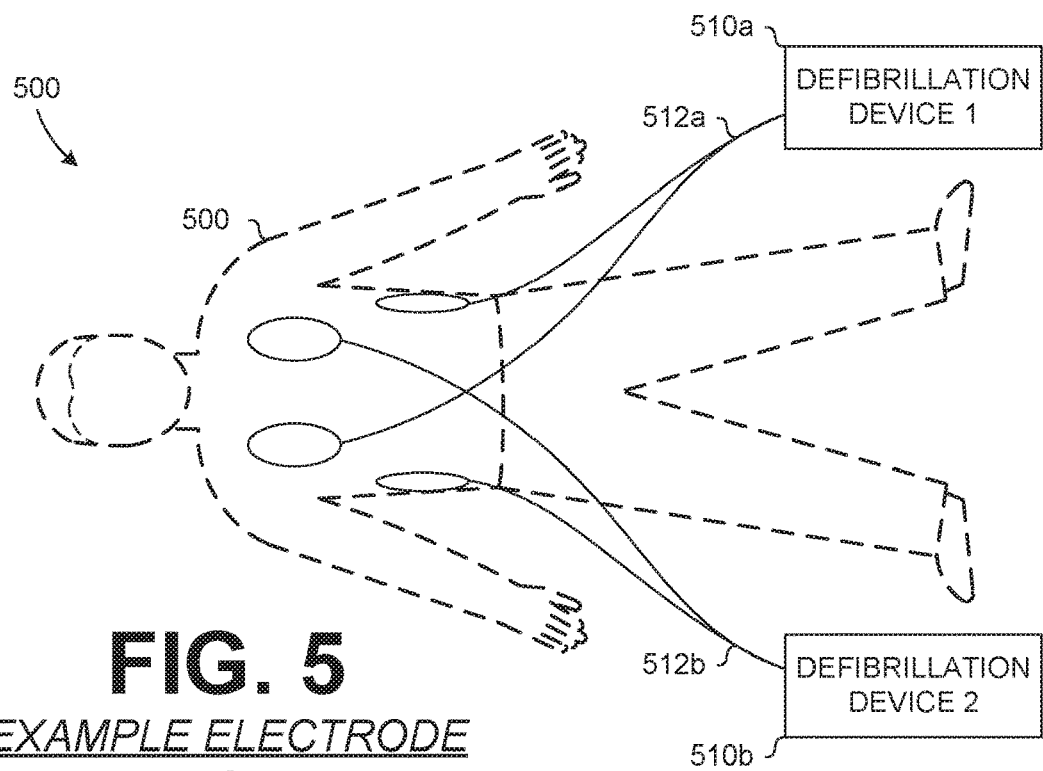
FIG. 5  *EXAMPLE ELECTRODE ARRANGEMENT*

*EXAMPLE SHOCK VECTOR SYSTEM*

*EXAMPLE ELECTRODE ARRANGEMENT*

SYSTEMS AND METHODS FOR DOUBLE SEQUENTIAL DEFIBRILLATION

CROSS-REFERENCE TO RELATED APPLICATIONS

This application claims the benefit of U.S. Provisional Patent Application Ser. No. 62/431,408, filed on Dec. 7, 2016, the contents of which are herein incorporated by reference in their entirety.

BACKGROUND

Double sequential defibrillation (DSD), also sometimes referred to as dual simultaneous defibrillation, is a treatment protocol that is growing in use and popularity to treat patients suffering from cardiac arrest. For a patient in ventricular fibrillation, and especially for a patient suffering from recurrent and uncontrolled ventricular fibrillation, the use of DSD or simultaneous defibrillation can be an effective treatment in restoring the patient's normal heart rhythm. DSD is considered by rescuers as a desperate last ditch effort to save the life of a cardiac arrest victim. Administration of DSD can be haphazard, poorly timed, and uncoordinated. DSD involves simultaneous defibrillation administered using two separate defibrillators, of the same or distinct types, such as an automated external defibrillator (AED) and/or a standard defibrillator or monitor/defibrillator. As DSD is currently practiced, human rescuers typically attempt to manually time the two (or more) defibrillation shocks to be delivered to the patient at as close to the same time as possible. However, due to the extremely short duration of the defibrillation pulses, and the limits of human temporal perception and motor control, in practice every pair of DSD shocks will have a slightly different timing. This variation in timing of the two shocks can impact both the efficacy and the safety of the DSD procedure.

Relying on human ability and/or judgment to administer shocks from two separate defibrillators in a coordinated manner is thus an imperfect system that can result in ineffective therapy outcomes due to improper shock delivery timing.

DSD and simultaneous defibrillation is becoming more widely adopted as a treatment for patients suffering from cardiac arrest. Presently, there is a need for a solution that would assist in proper delivery of DSD therapies that are efficient, safe, and effective.

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 4 is a block diagram of an example defibrillation device.

FIG. 5 illustrates an example arrangement of multiple defibrillation devices on a patient.

DETAILED DESCRIPTION

Figure 3:
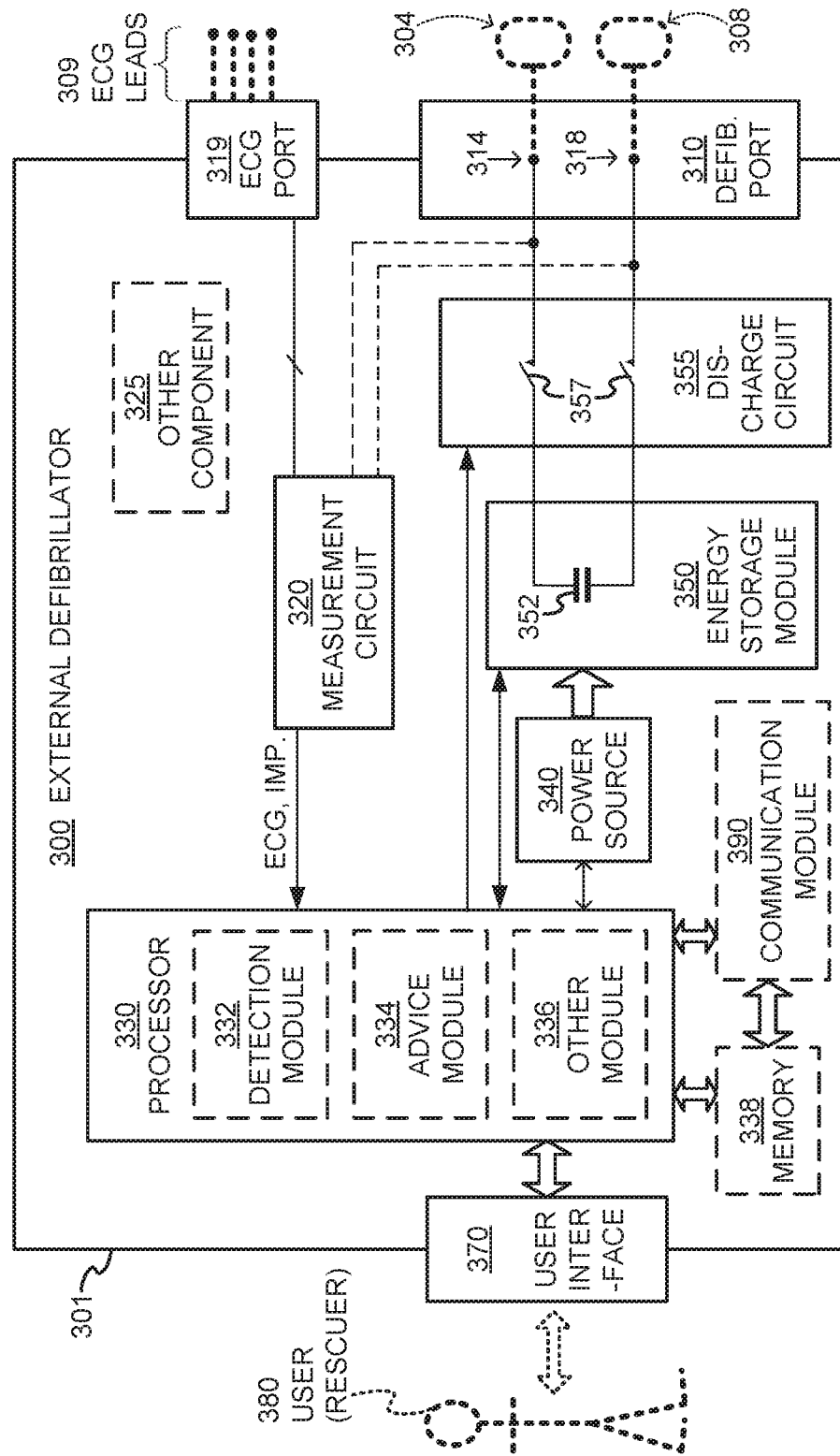
FIG. 3 is a functional block diagram showing components of an external defibrillator, such as the one shown in FIG. 1.

Described herein are methods and systems for controlling multiple defibrillation therapies, such as double sequential defibrillation (DSD), also known as dual simultaneous defibrillation. DSD is the administration of multiple defibrillation therapies, shocks, or energy deliveries, substantially concurrently with each other. Within the limits of human perception and motor control, these multiple shocks typically are perceived to be delivered simultaneously or in rapid succession. In practice, DSD results in a range of timing relationships between the two or more shocks, and the precise timing relationship achieved for any given DSD treatment is both unable to be controlled, and unable to be measured, by a human operator. The administration of multiple defibrillations and/or energy therapies has been used to assist with correcting an abnormal heart rhythm of patients experiencing a cardiac arrest, such as an arrhythmia or more specifically refractory ventricular fibrillation or refractory atrial fibrillation. The systems and methods described below provide a controlled, adjustable and repeatable means for delivery of such defibrillation therapies so as to assist in the correction of an abnormal heart rhythm. FIGS. 1-3 explain a general overview of defibrillation therapy using a single defibrillation or therapy module for sake of simplifying the general explanation. FIGS. 4-7 relate specifically to DSD and/or simultaneous defibrillation using two or more therapy modules and/or defibrillators.

FIG. 1 is a diagram of a defibrillation scene in which a patient is receiving defibrillation therapy from a single external defibrillator 100. The person 82 is lying on his or her back and could be a patient in a hospital, or someone found unconscious, and then turned to be on their back. The person 82 is experiencing a cardiac arrhythmia in his or her heart 85, which could be Ventricular Fibrillation (VF) for example.

A portable external defibrillator 100 has been brought close to the person 82. At least two defibrillation electrodes 104, 108 are usually provided with an external defibrillator 100, and are sometimes called electrodes 104, 108. The electrodes 104, 108 are coupled with the external defibrillator 100 via respective electrode leads 105, 109. A rescuer (not shown) has attached electrodes 104, 108 to the skin of person 82 and actuates the defibrillator 100 to administer a brief, strong electric pulse 111 via electrodes 104, 108 through the body of person 82. Pulse 111, also known as a defibrillation shock, goes also through heart 85, in an attempt to restart it by depolarizing the cardiac cells and resetting the natural pace for the heart, for saving the life of the person 82.

The defibrillator 100 can be one of different types, each with different sets of features and capabilities. The set of capabilities of the defibrillator 100 is determined by planning who would use it, and the training those rescuers would be likely to have. Examples are now described.

FIG. 2 is a table listing two main types of external defibrillators, and their primary users. A first type of defibrillator 100 is generally called a defibrillator-monitor because it is typically formed as a single defibrillation unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. and often requires technical training on its operation. Such a defibrillator-monitor is intended to be used in a pre-hospital or hospital scenario.

As a defibrillator, the device can be one of different varieties, or even versatile enough to be able to switch among different modes that individually correspond to the device varieties. One variety is that of an automated defibrillator, which can determine whether a shock is needed and, if so, charge a therapy module of the device to a predetermined energy level and instruct and/or prompt the user to administer the shock. Another variety is that of a manual defibrillator where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signal or impedance between two electrodes. Additionally, these signals can relate to the person's temperature, non-invasive blood pressure (NIBP), arterial oxygen saturation/pulse oximetry ($SpO_2$), the concentration or partial pressure of carbon dioxide in the respiratory gases, known as capnography, and so on. These signals can be further stored and/or transmitted as patient data.

A second type of external defibrillator 100 is generally called an AED, which stands for "Automated External Defibrillator". An AED typically automatically makes the shock/no shock determination on whether to deliver defibrillation therapy to the patient. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, hospitals, for example, may deploy AEDs at its various floors, in case the more expensive defibrillator-monitor is more critically being deployed at an Intensive Care Unit or other emergency situation of greater need, and so on.

AEDs, however, can also be used by people who are not in the medical profession. More particularly, an AED can be used by many professional first responders, such as the police, firefighters, emergency medical personnel, etc. AEDs are often found in public locations especially those locations that tend to host large numbers of people. Such AEDs are often operated by rescuers with first-aid training or by a good Samaritan who has no training on the device at all. AEDs increasingly can supply instructions to whoever is using them and anticipate this wide variety of skill levels of its users.

AEDs are thus particularly useful because clinical response time is very critical when responding to someone suffering VF. Indeed, the people who are able to first reach the VF sufferer may not be and are often not in the medical professions.

There are additional types of external defibrillators that are not listed in FIG. 2. For example, a hybrid defibrillator can have aspects of an AED and also of a defibrillator-monitor. A usual such aspect is additional ECG monitoring capability among others.

FIG. 3 is a diagram showing components of an external defibrillator 300 made according to embodiments. These components can be, for example, in the external defibrillator 100 of FIG. 1. Additionally, the components of FIG. 3 can be provided in a housing 301, which can also be known as a casing 301. The external defibrillator 300 is intended for use by a user 380, who is the rescuer. The defibrillator 300 typically includes a defibrillation port 310, such as a socket in the housing 301. The defibrillation port 310 includes nodes 314, 318. The defibrillation electrodes 304, 308, which can be similar to the electrodes 104, 108, can be connected to the defibrillation port 310 so as to make an electrical connection with the nodes 314, 318, respectively.

It is also possible that electrodes can be connected continuously to the defibrillation port 310, etc. Either way, the defibrillation port 310 can be used for guiding an electrical charge that has been stored in the defibrillator 300 to the person 82 through the electrodes.

If the defibrillator 300 is a defibrillator-monitor, as was described with reference to an example discussed in FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and another component 325 structured to filter the ECG signal, e.g., apply at least one filter to the signal so as to remove chest compression artifacts resulting from chest compressions being delivered to the person 82. The defibrillator 300 shown in FIG. 3 also includes a measurement circuit 320 that receives patient physiological signal(s) from the ECG port 319, and also from other ports, if provided. These physiological signals are sensed, and information about them is rendered by the circuit 320 as data, or other signals, etc.

If the defibrillator 300 is an AED, it may lack an ECG port 319. The measurement circuit 320 can obtain physiological signals through nodes 314, 318 instead, when defibrillation electrodes 304, 308 are attached to person 82. In these examples, a patient's ECG signal can be sensed as a voltage difference between the electrodes 304, 308. Further, impedance values sensed between the electrodes 304, 308 can be detect, among other things, whether these electrodes 304, 308 have been inadvertently disconnected from the person.

The defibrillator 300 also includes a processor 330 that may be implemented in any number of ways. Such ways include, by way of example and not limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 330 can include a number of modules. One such module is a detection module 332, which senses outputs of measurement circuit 320. Detection module 332 can include a VF detector. Thus, the person's sensed ECG can be used to determine whether the person is experiencing VF. Another such module in the processor 330 is an advice module 334, which arrives at advice based on output(s) of the detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report the shock recommendation to the user, and prompt them to do it. Other embodiments further execute the advice, by administering the shock. If the advice is to administer CPR, the defibrillator 300 may further issue prompts for it, and so on. The processor 330 can include additional modules, such as the module 336, for other functions. In addition, if another component 325 is indeed provided, it may be operated in part by the processor 330, etc.

Defibrillator 300 optionally further includes a memory 338, which can work together with the processor 330. The memory 338 may be implemented in any number of ways. Such ways include, by way of example and not of limitation, nonvolatile memories (NVM), read-only memories (ROM), random access memories (RAM), any combination of these, and so on. The memory 338, if provided, can include programs for the processor 330, and so on. The programs can be operational for the inherent needs of the processor 330, and can also include protocols and ways that decisions can be made by the advice module 334. In addition, the memory 338 can store prompts for the user 380 and patient data, as needed.

The defibrillator 300 may also include a power source 340. To enable portability of the defibrillator 300, the power source 340 typically includes a battery. Such a battery can be implemented as a battery pack, which may be rechargeable or not. Sometimes, a combination is used, of rechargeable and non-rechargeable battery packs. Other embodiments of power source 340 can include AC power override that allows a rescuer to use AC power when such a source exists, but rely on the battery power if AC power is unavailable. In some embodiments, the power source 340 is controlled by the processor 330. The defibrillator 300 additionally includes an energy storage module 350. The module 350 is where some electrical energy is stored, when preparing the device for sudden discharge to administer defibrillation shock therapy to the patient. The module 350 can be charged from the power source 340 to the desired amount of energy, as controlled by the processor 330. In typical implementations, the module 350 includes one or more capacitors 352 that charge and help store the energy for later discharge, and so on.

The defibrillator 300 can also include a discharge circuit 355. The discharge circuit 355 can be controlled to permit the energy stored in the module 350 for discharge to the nodes 314, 318, and thus also to the defibrillation electrodes 304, 308. The discharge circuit 355 can include one or more switches 357. Those switches can be made in a number of ways, such as by an H-bridge, and so on, or other desirable configurations.

The defibrillator 300 further includes a user interface 370 for the user 380. For example, the interface 370 may include a screen to display what is detected and measured, provide visual feedback to the rescuer for their resuscitation attempts, and so on. The interface 370 may also include a speaker to issue voice prompts or otherwise audibly interact with the user and may additionally include various controls, such as pushbuttons, keyboards, and so on, as needed or desired. In addition, the discharge circuit 355 can be controlled by the processor 330, or directly by the user 380 through the user interface 370.

The defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and the like. Another feature of a defibrillator can be CPR-prompting in which prompts are issued to the user, visual or by sound or otherwise, so that the user can administer CPR and/or receive feedback/instructions regarding the administration of CPR and/or delivery of shock therapy to the patient.

FIG. 4 is an example defibrillator/defibrillation device 400 that can be used for administration of a DSD, or other, therapy. The defibrillation device 400 can include, and/or be connected to, various systems and/or components such as an input/output module 410, a communication module 420, a physiological parameter module 430, a thermoregulation module 440, a control module 450, a therapy module 460, an energy storage module 470, a maintenance module 480 and/or other modules/components. The duties and/or functions of the defibrillation device 400 can be performed by one or more modules, systems and/or components of the defibrillation device 400. Additionally, data, functions and/or capabilities of the various modules, systems and/or components of the defibrillation device 400 can be performed by and/or shared with one or more modules, systems and/or components of the defibrillation device 400 to perform the necessary and/or desired functions of the defibrillation device 400. Alternatively, one or more data, functions and/or capabilities of the various modules, systems and/or components of the defibrillation device 400 can be performed by and/or shared with one or more external devices, systems and/or networks that can be communicatively coupled to the defibrillation device 400.

The input/output module 410 can include inputs and/or outputs so that the defibrillation device 400 can receive and/or transmit information in a visual 412, audio 414 and/or tactile 416 format. For example, the input/output module 410 can include a display, to relay visual 412 data, and a speaker, to relay audio 414 data, to a user. The display can also be a touchscreen to allow a user to input tactile 416 data to the defibrillation device 400. For other example outputs, other visual 412 indicators can include one or more lights and/or visual displays and other audio 414 indicators can include one or more device capable of transmitting audible and/or inaudible audio data. Tactile 416 output indicators can include haptic feedback and/or systems/devices for providing tactile response to a user. Example visual 412 inputs can include a camera, capable of visible and/or non-visible light capture, and example audio 414 inputs can include one or more microphones for capturing audible and/or inaudible sounds. Tactile 416 inputs can include user actuatable inputs, such as switches, buttons and/or touch sensitive inputs. The input/output module 410 can allow the defibrillation device 400 to transmit and/or receive information to/from a user or other person(s).

The communication module 420 can facilitate communication between the defibrillation device 400 and other devices, systems and/or networks. Data can be transmitted and/or received by the defibrillation device 400 via the communication module 420. The communication module 420 can include various hardware and/or software to facilitate communication via one or more communication protocols, such as a cellular network, a Wi-Fi network and/or Bluetooth®. Communications via the communication module 420 can be encrypted to prevent collection of the transmitted information. Additionally, the communication module 420 can facilitate data transmission via one or more protocols and/or with one or more devices/systems substantially simultaneously. Further, the communication module 420 can include functionality to detect devices, systems and/or networks within a proximity of the defibrillation device 400 and can notify a user of the device, system and/or network and/or automatically connect and/or prompt a user to connect to the detected device, system and/or network.

An example device, system and/or network that can be communicatively coupled to the defibrillation device 400, via the communication module 420, can include a remote processing and/or control device, system and/or network. In an embodiment, the remote processing and/or control can receive physiological data from the defibrillation device 400, and/or from another source, and can determine whether an electrotherapy administration is needed, such as a DSD therapy. The remote processing and/or control can also control one or more defibrillation devices, such as 400, to coordinate the delivery of a multiple electrotherapy administration, such as a DSD therapy. The control can include triggering the one or more defibrillation devices to enter one or more protocols depending on the electrotherapy to be administered, triggering the administration of an electrotherapy from the one or more defibrillation devices and/or prompting a user to perform various steps/procedures to prepare and/or administer an electrotherapy from the one or more defibrillation devices.

The physiological parameter module 430 can receive, analyze and/or process various patient physiological parameters and/or data. The physiological parameter data can be used to select and/or adjust a therapy administered by the defibrillation device 400 and/or to monitor the patient and their status. Various sensors, such as electrodes, can be connected to the patient to collect physiological data that can be received by the physiological parameter module 430. Physiological data can also be collected by other sensors, devices and/or systems separate from the defibrillation device 400 and can be transmitted to and/or received by the physiological parameter module 430. The physiological parameter module 430 can transmit the physiological data, and/or the analysis thereof, to various other components and/or modules of the defibrillation device 400 and/or with external devices and/or systems.

The thermoregulation module 440 can include various components and/or systems for regulating the temperature of the defibrillation device 400 and/or components/systems thereof. The defibrillation device 400 can include one or more thermoregulation devices and/or systems that can be controlled by and/or integrated with the thermoregulation module 440 to regulate the temperature of one or more components, modules and/or systems of the defibrillation device 400. Various thermoregulation devices and/or systems can include heating and/or cooling systems and devices, such as thermoelectric devices. Thermal regulation of components of the defibrillation device 400 can prolong their usable lifespan and/or prevent damage of the defibrillation device 400 caused by the administration of electrotherapies.

The control module 450 can be connected to various other components, modules and/or systems of the defibrillation device 400 and can control various functions of the defibrillation device 400. The control module 450 can include memory 452 for storing instructions and/or data and a processor 454 for controlling and/or executing the various functions of the defibrillation device 400. A record of the various functions, such as administration of a therapy, by the defibrillation device 400 can be stored in the memory 452. This record can be accessed and/or retrieved to review the past functioning and use of the defibrillation device 400. Data stored by the defibrillation device 400 can include other data, such as physiological parameter data of a patient, annotations and/or other data, which can be correlated to the functioning/use of the defibrillation device 400.

The therapy module 460 can include various components and/or systems to assist with transmitting electrical energy to a patient to which the defibrillation device 400 is connected. The therapy module 460 can include a therapy circuit for delivering a controlled and/or specified electrical charge, having one or more energy characteristics, to the patient. Electrodes, and/or other patient interface devices, can be coupled to the therapy module 460 to transmit the electrical charge from the therapy module 460 to the patient.

The power module 470 can include one or more energy storage devices and/or power inputs. An example power storage device can include a battery for powering the functions and abilities of the defibrillation device 400 when the device 400 is not connected to a power source. The power module 470 can also include a power input to connect the defibrillation device 400 to an external power source, such as an external battery or a wall outlet, for powering the function and abilities of the defibrillation device 400. As with the other described modules and/or systems, in some embodiments, the power module 470 can be removable/interchangeable from the defibrillation device 400, allowing a different power module 470 to be connected to the defibrillation device 400.

The maintenance module 480 can include various systems and/or processes for maintaining and/or verifying the functionality of the defibrillation device 400, its components, modules and/or systems. For example, the maintenance module 480 can include self-test processes for validating and/or assessing the functionality of the defibrillation device 400. Additionally, the maintenance module 480 can include storage for recording the results of the assessments of the functioning of the defibrillation device 400 and/or maintenance performed by a user, or other, on the defibrillation device 400.

The defibrillation device 400, discussed above, can be used to assist in administering DSD and other electrotherapies. This assistance can include assessment prior to application of a therapy to determine the need for electrotherapy, or the appropriate electrotherapy to administer, and can also include assessment after application of the electrotherapy to determine its efficacy and to determine if further electrotherapy is needed. The defibrillation device 400, and its various components, modules and/or systems, can assist a user with making various assessments and determinations with regards to an electrotherapy treatment of a patient.

FIG. 5 illustrates an example arrangement 500 of multiple defibrillation devices 510*a*, 510*b* that are connected to a patient 502 via electrodes pairs 512*a*, 512*b*. The arrangement 500 can be used in the administration of a DSD, and/or other, electrotherapy to the patient 502.

In an example embodiment, the defibrillation device 400 can include an input/output module 410 having a display screen as a visual 412 output. Physiological data, such as from the physiological parameter module 430, of a patient can be displayed on the display screen to allow a user, such as a rescuer or physician, to visualize various data regarding the patient and the physiology. The patient physiological data shown on the display screen can include an electrocardiogram (ECG) waveform of the patient. Additionally, the display screen can include a touch interface allowing a user to interact with the defibrillation device 400 via the display screen. Alternatively, other user interface controls can be included on the display screen, the defibrillation device 400, or externally from the defibrillation device 400, to allow the user to interact with the defibrillation device 400. In an example, the user interaction with the defibrillation device 400 can allow the user to pause and/or review previous ECG waveform data, such as by "swiping," or gesturing, on the display screen to scroll or move back through the ECG waveform to a prior point. In another example, the user can select a rewind function that can automatically recall and/or display a previous portion of the ECG waveform, such as a predetermined duration of the ECG waveform or the ECG waveform after an event, including an electrotherapy administration. The ECG waveform review functionality can allow a user to review the ECG waveform of the patient to assess the efficacy and/or results of an electrotherapy administration. The portion of the ECG waveform being reviewed can be displayed concurrently with the current ECG waveform to allow the user to review the past ECG waveform while continuing to monitor the patient's current ECG waveform.

The displayed ECG waveform(s) can be filtered, automatically or as needed, such as to remove artifacts that may have been introduced by other patient procedures, including cardiopulmonary resuscitation (CPR). The input/output module 410, the physiological parameter module 430, the control module 430, or another system, component and/or module of the defibrillation device 400, can include filtering circuitry and/or software to assist with the filtering of the ECG waveform. While the display screen has been described as integrated with the defibrillation device 400, the display screen can be remote and/or separate from the defibrillation device, with the data to be displayed on the display screen being communicated to the display screen, such as by a physical or wireless connection. Alternatively, the display screen can be a display screen of another device, such as a tablet computer, that is communicatively coupled to the defibrillation device 400 to display data on the display screen.

The review of a patient's ECG waveform after administration of an electrotherapy can assist a defibrillation device 400 user, or other person or device, in determining whether a DSD electrotherapy is warranted and/or needed. For a patient in ventricular fibrillation (VF), an electrotherapy can be administered to correct the abnormal cardiac rhythm. A review of a portion of the patient's ECG waveform immediately after the administration of the electrotherapy can indicate to the user whether the patient continues to be in a VF state or whether the patient's cardiac rhythm was corrected from a VF state but has proceeded back to a VF state. In an example embodiment, the control module 450 of the defibrillation device can permit the review of and/or provide the stored ECG data for review by a user, by one or more modules/systems of the defibrillation device, such as the control module itself, and/or by an external device, system and/or network. In an embodiment, the control module 450 can determine that a multiple electrotherapy administration is warranted, or a probability of such administration being warranted, and can provide ECG data for review by a user, the defibrillation device and/or an external source. The review of the ECG data, by the user, the defibrillation device and/or an external source, can determine one or more electrotherapy administrations, such as a DSD therapy. For example, if the ECG waveform indicates the patient's VF state has continued despite the administration of an electrotherapy, then the patient may be experiencing refractory VF and a DSD, or other, electrotherapy may be warranted and/or needed to assist in correcting the patient's abnormal cardiac rhythm. If the ECG waveform indicates the patient transitioned from a VF state but has subsequently reverted to a VF state, then the administered electrotherapy was successful temporarily in correcting the VF of the patient and a further, non-DSD, electrotherapy may be warranted and/or needed to correct the patient's abnormal cardiac rhythm. The review of the ECG waveform immediately after an electrotherapy administration can help prevent the undue administration of a DSD therapy when it may be unwarranted and/or unneeded.

In an example, the defibrillation device can generate a record and/or list of electrotherapy shocks administered to a patient thus far during a resuscitation attempt, along with information indicating whether or not each shock successfully terminated VF. This information can be displayed or otherwise relayed to a user, an external device, an external system, an external network, or a combination thereof. The record can include various information that can be in the form of a segment of the ECG waveform taken from immediately after, and optionally also before, delivery of each shock, and/or in the form of an automated algorithm that processes the ECG waveform, including filtering of any chest compression artifact, and then automatically determines and displays, for each shock, whether VF was or was not successfully terminated. Such functionality would allow a user, or other, to review the efficacy of the defibrillation shocks administered to a patient thus far, and can assist in making a determination of whether or not an attempt at DSD may be warranted in that patient. The record describing all defibrillation shocks, and whether or not they successfully terminated VF, could be in the form of an itemized list of each shock, or could be summarized to varying degrees, such as displaying a tally of successful and unsuccessful shocks, or simply displaying an indication of whether or not any shocks delivered thus far have successfully terminated VF. The record can be continuously presented to a user, such as by a display of the defibrillation device, or could be selected by the user, via user interface controls, for temporary display at a desired time point during the patient care event.

The display screen can also display additional patient monitoring and/or physiological data from the defibrillation device 400 and/or another source, such as another device and/or system. For example, after a DSD therapy administration, an ultrasound image, or video, of the patient's heart can be captured and displayed on the display screen. A user can review the ultrasound image to visualize the motion of the patient's heart walls and/or the ultrasound image can be analyzed for motion of the patient's heart walls for indications of one or more cardiac rhythms present in the ultrasound image. The analysis and/or review of the ultrasound image can assist with making a determination of the cardiac rhythm of the patient, as displayed in the ultrasound image.

Recording the actions and/or information of the defibrillation device 400 can serve as a useful tool in assessing the performance of the defibrillation device 400 and/or a user. The defibrillation device 400 can include components, systems and/or modules, such as the control module 450 or the communication module 420, to allow such recording of the information to take place. Additionally, maintenance performed, such as by the maintenance module 480, on and/or by the defibrillation device 400 can be recorded to assess the functioning and/or abilities of the defibrillation device 400. For example, after administration of a DSD or other electrotherapy, the defibrillation device 400 can perform a self-test, such as by the maintenance module 480, to assess the functioning of the defibrillation device 400 post-electrotherapy administration. The self-test can be performed at a time and/or in a manner so as not to impair the functioning and/or use of the defibrillation device 400, such as being performed at a later time when a patient event the defibrillation device 400 is being used to treat has ended. Assessment of the functioning of the defibrillation device 400 can assist with determining if the defibrillation device is in a state for later use, requires maintenance, in need of repair before next use and/or other assessable states/criterion.

DSD and/or other electrotherapy administrations can be recorded and/or stored using the defibrillation device 400. In some embodiments, the defibrillation device 400 can record and/or store a record of various events and/or the defibrillation device 400 can communicate with an external device/system to record and/or store a record of the events. The recording of an electrotherapy administration can include recording the identity of the defibrillation device 400, patient physiological data collected during the treatment, characteristics of the one or more electrotherapies administered and/or other data regarding the treatment of the patient.

The recorded information can be transmitted to an external system, such as a manufacturer data collection system, device administrator data collection system and/or other data collection systems, such as for tracking the use, maintenance and/or functionality of the defibrillation device 400. Additional information that can be recorded and/or transmitted can include self-test and/or maintenance data for the defibrillation device 400 after administration of an electrotherapy. The defibrillation device 400 and/or a remote device/system can track the usage of the defibrillation device 400 for potential billing, maintenance and/or repair issues, such as tracking the DSD therapy usage of the defibrillation device. Administration of DSD and/or other electrotherapies can cause wear to one or more components, systems and/or modules of the defibrillation device 400. Usage of the defibrillation device 400 can be monitored to facilitate preemptive maintenance, such as replacement of components, of the defibrillation device 400 based on usage of the device 400. The usage data can also be used to confirm valid and/or appropriate usage of the defibrillation device 400, such as usage that complies with the usage terms in the warranty and/or contract of the defibrillation device 400.

The recordation and/or collection of defibrillation device 400 data can allow for a review of the efficacy of electrotherapy administration in the various treatment situations in which the defibrillation device 400 was used. In an example, for a patient who undergoes a DSD therapy, the patient's physiological, and/or other, data can be reviewed, such as to assess the efficacy of the DSD therapy and to improve future administrations of DSD therapies. The collected data can be compiled to define and/or refine procedures and indications for the administration of DSD and/or other electrotherapies.

For use in a DSD therapy administration, one or both of the defibrillation devices used, such as the defibrillation device 400, can include software and/or hardware to assist with preventing electrotherapy discharge from one defibrillation device causing damage to the other defibrillation device. In an example, the electrotherapy discharge from each defibrillation device can be coupled so as to discharge the second electrotherapy with a specific timing relative to the discharge of the first electrotherapy. The coupling can be set manually by a user, or other person or device, or can be determined and/or set automatically by one or more of the defibrillation device(s), an external device and/or an external system. Various factors can influence the coupling and/or timing of the electrotherapy administrations, such as the abilities, functions and/or status of one or more of the defibrillation devices being used to perform the DSD administration, the patient physiological parameters, and/or other factors relevant to the administration of the DSD therapy. Status of the defibrillation device can include status of one or more components/systems of the defibrillation device, such as the state of an output relay of the defibrillation device. The coupling can prevent both defibrillation devices from having their respective output relays closed at the same time. Alternatively, the coupling can allow the respective output relays to be closed at the same time but control internal switching devices in such ways as to not allow delivery of defibrillating current to flow from both defibrillation devices at the same time. In another version of this later embodiment, the coupling can further allow phases of the discharge from the two devices to be interleaved.

The coupling between defibrillation devices can be a physical and/or a wireless connection, such as can be facilitated by the communication module 420 of the defibrillation device 400. The communicatively coupled defibrillation devices can have a functionality/capability and/or risk assessment to assist with determining which, if either, defibrillation device may be at more risk of damage by administration of a DSD therapy. The assessment can be based on a predetermined arrangement, i.e. one defibrillation device communicates to the other its order in a DSD electrotherapy administration, using an algorithm and/or by other assessment means that can include various data/information regarding one or more of the defibrillation devices to be used. Using the assessment, the defibrillation devices can have a priority, such as an order in the DSD electrotherapy administration or a safeguard priority to prevent damage to the device. In an example in which the defibrillation devices to be used to administer DSD therapy are an AED and an advanced monitor/defibrillator, the assessment may determine that the advanced monitor/defibrillator needs to have potential damage risks minimized during DSD administration since the advanced monitor/defibrillator has advanced capabilities for treating and/or monitoring the patient.

To assist with reducing risk to the one or more defibrillation devices used to administer a DSD therapy, the discharge from each defibrillation device can have a modified waveform from the waveform normally associated with a defibrillation discharge. One or more of the defibrillation devices can receive information, such as by a user, and/or detect the other defibrillation device attached to a patient who will receive the DSD treatment. Based on the indication of another defibrillation device, one or more of the defibrillation devices can operate in a DSD mode that can modify the waveform of the discharge from the defibrillation device. The waveform modification of the discharge can be predetermined, selected and/or automatically determined based on various parameters, such as the abilities/functions of the defibrillation device(s) and/or the potential risk to the defibrillation device(s) due to the DSD therapy administration. In an example embodiment, modification of a discharge waveform can include discharging a monophasic waveform instead of a biphasic waveform. The monophasic waveform discharge can require a reduced number of switching events by the defibrillation device, its components and/or systems, to output the monophasic waveform. The reduction of switching events can prevent damage to one or more switching elements of the defibrillation device(s) used in the DSD therapy administration. Additionally, the waveform of the discharge can be shortened to reduce the duration during which the defibrillation device(s) can be vulnerable to damage by the discharge of one or more of the defibrillation device(s). Additionally, the interval between phases of a multiphasic waveform of one defibrillator can be lengthened to allow time for delivery of a phase by the other defibrillator.

In another example, a defibrillation device can include protection circuitry and/or software to assist with protecting the defibrillation devices, such as 400, during the administration of DSD and/or electrotherapies. For example, the defibrillation device can include a protection circuit and/or module that can be a separate component and/or integrated with another component, module and/or system of the defibrillation device, such as the therapy module 460. The protection circuitry can prevent and/or reduce feedback of discharge energy into the defibrillation device. Protection software can modify the functioning of the defibrillation device to assist with reducing potential damage to the defibrillation device by the administration of an electrotherapy. For example, in a DSD therapy, the protection software can reduce and/or minimize the duration of switching in the administration of an electrotherapy by the defibrillation device. As discussed, the reduction in switching can assist preventing damage to the defibrillation device but may be undesirable during routine operation as a stand-alone defibrillator.

Thermoregulation of a defibrillation device, its components and/or systems, can also be used to reduce potential damage to the defibrillation device by the administration of an electrotherapy, such as a DSD therapy. The defibrillation device can include a thermoregulation module, such as 440, and/or other thermoregulation systems/elements to assist in regulating the temperature of one or more components/systems of the defibrillation device. In an example embodiment, thermoregulation of the switching elements/components of the defibrillation device can assist with preventing and/or reducing damage to the switching elements by an electrotherapy administration. Depending on a mode, an electrotherapy treatment to be administered, or not, the switching elements of the defibrillation device can be cooled during a time period during which they are vulnerable to damage by an electrotherapy administration. The switching elements can be cooled to prevent their overheating, such as by thermoelectric elements, a refrigeration system/element, a cooling spray and/or other cooling systems, elements, or methods. The defibrillation device can automatically initiate the cooling of the switching elements, such as in response to a selected electrotherapy, the detection of another defibrillation device, an electrotherapy discharge and/or other factors. Cooling, or thermoregulation, of the switching elements can be performed as long as required based on one or more electrotherapy administration factors, such as the duration of the electrotherapy administration or the sensed temperature of the switching elements. For a cooling spray, the defibrillation device can cause the cooling spray to be dispensed onto the switching elements as needed, or required. Example cooling sprays can include compressed gases/liquids, gases/liquids having a desired thermal capacity, and/or other suitable fluids capable of accepting thermal energy from the switching elements. As part of the thermal regulation, various components and/or systems of the defibrillation can be thermally monitored and/or regulated to assess an expected operable lifetime of the component and/or system. The thermal regulation of the components and/or systems can extend an operable lifetime of the component/system and/or assist with maintaining a functionality/ability capacity of the defibrillation device to administer electrotherapies.

As part of increasing and/or maintaining a robustness and/or functionality of a defibrillation device, the components and/or systems of the defibrillation device can be designed and/or selected to have an increased usage tolerance. The increased usage tolerance of the defibrillation device can assist the device in safely operating in conditions that might otherwise potentially damage the defibrillation device. For example, an increased safety factor can be used in designing and/or selecting components/systems, such as critical components/systems, to assist with increasing the robustness and/or maintaining functionality of the defibrillation device.

The defibrillation device can also include various functionality, such as hardware and/or software implemented functionality and/or access to remote functionality, to assess a patient's need for DSD and/or other electrotherapies. For example, the defibrillation device can detect refractory VF after one or more shock, or electrotherapy, administrations. After detecting the refractory VF, the defibrillation device can alert a user and indicate that a DSD therapy administration may be warranted. The user can then select to begin a DSD protocol and/or administer DSD therapy in response to the detected refractory VF. As part of the DSD protocol, the defibrillation device can request user confirmation of refractory VF and/or confirmation to administer a DSD therapy. Alternatively, the defibrillation device can initiate a DSD therapy automatically in response to the detected refractory VF. The defibrillation device can consider various physiological parameters and/or data to determine the presence of refractory VF.

Refractory VF can occur, or may continue, after administration of a DSD therapy and the defibrillation device can modify subsequent electrotherapies, including a DSD therapy, in response. For example, the defibrillation device can modify the DSD treatment to attempt to increase the efficacy of the DSD treatment. The modifications can include altering the coupling, or timing, between the shocks, changing the polarity of one or more of the shocks, changing one or more waveform characteristics of one or more of the shocks, and/or changing an energy level of one or more of the shocks. The indication of refractory VF after administration of a DSD therapy can also be indicated by a user to cause modification of the subsequent electrotherapy administration(s).

Additionally, the defibrillation device can use data, such as physiological parameters, to coordinate the delivery of an electrotherapy, including DSD therapy, with other factors that can influence the efficacy of the electrotherapy. For example, the electrotherapy delivery can be coordinated with ventilation of the patient. This can allow the electrotherapy to be administered at peak expiration, when the patient's lungs are empty, to increase the efficacy of the electrotherapy in correcting the cardiac rhythm of the patient. Peak expiration of the patient can be determined from various physiological parameters, such as an airway pressure or flow signal, an exhaled $CO_2$ waveform and/or a transthoracic impedance signal. The various physiological data can be collected by the defibrillation device, such as by the physiological parameter module 430, or otherwise communicated to the defibrillation device from one or more external devices and/or systems.

The DSD administration protocol of a defibrillation device can include provisions to cause one or more of the defibrillation devices, used in the DSD therapy, to administer their portion of the electrotherapy at a reduced energy. That is, the magnitude of the electrotherapy discharge by one or more the devices can be reduced. Additionally, the energy discharged by each defibrillation device of the DSD therapy administration can be the same or different. The initially reduced discharge can allow subsequent discharges to have a greater energy as needed and/or indicated by the presence of refractory VF. In this manner, follow-on administrations of DSD therapy can be administered in increasing energy levels to correct the abnormal cardiac rhythm, such as refractory VF, of the patient.

One or more of the defibrillation devices for use in a DSD therapy administration can be capable of detecting the presence of the other defibrillation device(s). This detection can include a determination that one or more of the defibrillation devices are using substantially the same impedance measurement signal frequency. The use of multiple defibrillation devices using the same impedance measurement signal frequency can cause interference that can alter the administration of an electrotherapy by a defibrillation device that bases its electrotherapy discharge on the detected impedance. In response to detecting the shared use of an impedance measurement signal frequency, one or more of the defibrillation devices can switch the frequency of their emitted impedance measurement signal to prevent the interference with other impedance measurement signals. The defibrillation devices can communicate to determine which device will switch the frequency of their impedance measurement signal or one or more of the defibrillation devices can include a protocol for switching frequency of their impedance measurement signal such that each defibrillation device connected to the patient emits impedance measurement signals on individual frequencies.

To coordinate the administration of electrotherapies from more than one defibrillation device, such as in a DSD therapy administration, the defibrillation device can include hardware and/or software to assist with and/or facilitate the coordinated delivery of the multiple electrotherapies. In an example, multiple defibrillation devices can be communicatively coupled, such as by a physical and/or a wireless connection, to allow one or more of the defibrillation devices to deliver individual electrotherapies in a coordinated manner, such as a DSD therapy. In another example, the defibrillation devices can be coupled by electromagnetic induction, with an electrotherapy discharge by a first defibrillation device causing an electromagnetic artifact to be generated and communicated, via the electromagnetic induction, to a second defibrillation device that can then administer an electrotherapy discharge in response to the received and/or detected electromagnetic artifact. In yet another example, the defibrillation devices could coordinate DSD by using the electrical conduction of the body of the patient to carry information, for example by modulation of the impedance signal carrier or a different high frequency.

In an example, the defibrillation devices may not be communicatively coupled but still able to deliver coordinated electrotherapies from each of the defibrillation devices. One of the defibrillation devices, connected to the patient, can be designated, manually or automatically, as a "slave" and operate in a "slave mode." As a "slave," the defibrillation device can monitor the patient, such as monitoring the patient's ECG and/or other physiological or physical pa-rameters, to detect an electrotherapy administration by another defibrillation device. Upon detection of the administered electrotherapy, the "slave" defibrillation device can administer an electrotherapy. The administered electrotherapy can be preselected and/or predetermined by the user, automatically based on physiological parameters and/or from/based on other inputs. Further, the administered electrotherapy can include various electrotherapy characteristics, including a duration, an intensity, a polarity, a relative timing of the administration based on the detected electrotherapy administration, and/or other factors contributing to the administration of the electrotherapy. The defibrillation device can include hardware and/or software to assist with the detection of a prior administered electrotherapy. Example hardware can include a variable impedance ECG input that can extend the dynamic range of the ECG signal and thereby allow accurate detection of high voltage transient signals associated with the administration of an electrotherapy while providing for the fast recovery of low voltage, high impedance signals, such signals being consistent with an ECG waveform. In an example embodiment, the defibrillation devices can include an AED and an advanced monitor/defibrillator, with the AED functioning as the first electrotherapy administration device and the advanced monitor/defibrillator acting as the "slave" device and administering an electrotherapy in response to the one administered by the AED. This kind of relationship between defibrillation devices does not require the communicative coupling of the devices, which can allow devices from different manufacturers, devices having different communication protocols and older devices incapable of communication to be used with a defibrillation device having a "slave mode" to achieve DSD and/or other electrotherapies.

In another example, a secondary device can be coupled to one or more defibrillation device to coordinate the administration of electrotherapies from each defibrillation device. The secondary device can be communicatively coupled to one or more of the defibrillation devices to control the administration of an electrotherapy from the coupled defibrillation device(s). In an embodiment, the secondary device can be a "sync box" that is coupled to both defibrillation devices so as to trigger an electrotherapy administration by each. The "sync box" can include programming and/or hardware to set a relative delay between the administration of electrotherapies by each of the defibrillation devices. The delay implemented by the "sync box" can be input manually by a user, input by an external device and/or system and/or automatically determined by the "sync box," such as by using physiological data collected from one or more of the defibrillation and/or other devices, systems and/or sources. The "sync box" can then trigger the administration of an electrotherapy by one or more of the connected defibrillation devices according to the delay, or timing relationship.

Alternatively, the "sync box" can function similarly to the "master-slave" device coordination described above. The "sync box" can be coupled to a defibrillation device designated as a "slave" and can sense an electrotherapy administration by the "master" defibrillation device to cause the "slave" device to administer an electrotherapy according to a timing relationship. In an example, a first defibrillation device can administer an electrotherapy and the "sync box" can detect, or otherwise determine, the administration of the electrotherapy. In response, the "sync box" can cause a connected defibrillation device to administer an electrotherapy. The administration of the electrotherapy by the connected defibrillation device can include various electrotherapy characteristics, such as an administration delay relative to the administered electrotherapy, a duration, an intensity and/or other characteristics.

Additionally, the "sync box" can account for various "critical to avoid" timings when determining a timing relationship between the administration of multiple electrotherapies. "Critical to avoid" timings can include timings that could compromise the physiologic efficacy of the administered electrotherapies, timing periods that have an increased potential for damaging one or more of the defibrillation devices and/or other timing considerations that could reduce the effectiveness of the administered electrotherapies and/or increase the potential of damaging one or more of the defibrillation devices. The "sync box" can consider one or more characteristics of one or more of the defibrillation devices when determining a "critical to avoid" timing to use. Further, the "sync box" can have, or have access to, various information regarding "critical to avoid" times for various defibrillation devices and/or physiological parameters/conditions.

The "sync box" can be physically, wirelessly, or otherwise coupled, to the one or more defibrillation devices for the coordinating the administration of electrotherapies. In an example, the "sync box" can connect directly to the hardware of a defibrillation device to initiate, or cause, the administration of an electrotherapy by the defibrillation device. In another example, the "sync box" can couple to the defibrillation device and use pre-existing hardware and/or software of the defibrillation device to cause the administration of an electrotherapy. For example, the "sync box" can be connected to a defibrillation device, such as an advanced defibrillator/monitor, that can monitor patient physiological parameters and can administer an electrotherapy in response to the detected physiological parameters. The "sync box" can be coupled to the advanced defibrillator/monitor and can output a signal, which mimics a physiological characteristic that would cause the advanced defibrillator/monitor to administer an electrotherapy, to then cause the advanced defibrillator/monitor to administer an electrotherapy.

In another example, the defibrillation devices can communicate and/or coordinate using respective impedance signals that each defibrillation device transmits. The defibrillation devices can modify one or more characteristics of their outputted impedance signals and these characteristics can be interpretable by the other defibrillation device to allow the defibrillation devices to communicate and/or coordinate. For example, the communicated data can be embedded in and/or superimposed on the outputted impedance signal of one defibrillation device and can be received and interpreted by another defibrillation device. In this manner, the defibrillation devices can coordinate their respective electrotherapy administrations.

A defibrillation device can also include an ability to couple with a mechanical CPR, or other, device. The coupling can include a defibrillation device that is integrated with a mechanical CPR, or other device, or a defibrillation device that is communicatively coupled so as to provide input or control to the mechanical CPR, or other, device. In an example, the defibrillation device can coordinate delivery of an electrotherapy, such as DSD, with the chest compressions administered by the mechanical CPR device. The defibrillation device can control, or otherwise cause, the mechanical CPR device to pause the administration of chest compressions, prior to, during and/or after the administration of an electrotherapy. The defibrillation device can also time, or cause, the administration of an electrotherapy during one or more phases of a chest compression cycle. Coordinating the administration of an electrotherapy with one or more phases of a chest compression cycle can allow the electrotherapy to be administered to have an increased efficacy than if the electrotherapy were administered during another phase, or phases, of the chest compression cycle. In the case of an integrated defibrillation device, the electrodes of the defibrillation device can be integrated with various components of the mechanical CPR device, such as an electrode integrated with the plunger and another electrode integrated with a back plate of the mechanical CPR device. Additionally, the defibrillation device and/or the mechanical CPR device can modify the administration of chest compressions prior to, during and/or after the administration of an electrotherapy. Such modification(s) to the chest compression administration can assist with the efficacy of the administered electrotherapy. In a further example, the mechanical CPR device can be instructed to deliver a precordial thump as part of an electrotherapy administration, such as a DSD therapy. In embodiments, the delivery of the precordial thump can be in addition to multiple electrotherapy administrations or in place of a subsequent electrotherapy administration of a multiple electrotherapy administration treatment.

In the coupling of multiple defibrillation devices, one of the defibrillation devices can include monitoring capabilities, such as an AED or a monitor/defibrillator, and the second, or subsequent, defibrillation device(s) can be simpler device that is capable of delivering an electrotherapy. The simpler device can include waveshaping circuitry and an electrotherapy charge device, such as a capacitor. The simpler device can be coupled to the other defibrillation device and can be caused to administer an electrotherapy, such as in response to and/or caused by the administration of an electrotherapy by the other defibrillation device. Alternatively, the initial electrotherapy administration can be by the simpler device and the other defibrillation device can administer an electrotherapy in response to the initial electrotherapy.

The electrotherapy administered by a defibrillation can include an electrical shock and the defibrillation device can include the ability, systems and/or components to deliver the shock along one or more specific shock vectors. The administration of one or more shocks along one or more shock vectors can be used in single shock electrotherapies and/or in multiple shock electrotherapies, such as DSD, that can use one or more defibrillation to deliver the multiple shocks.

Figure 6:
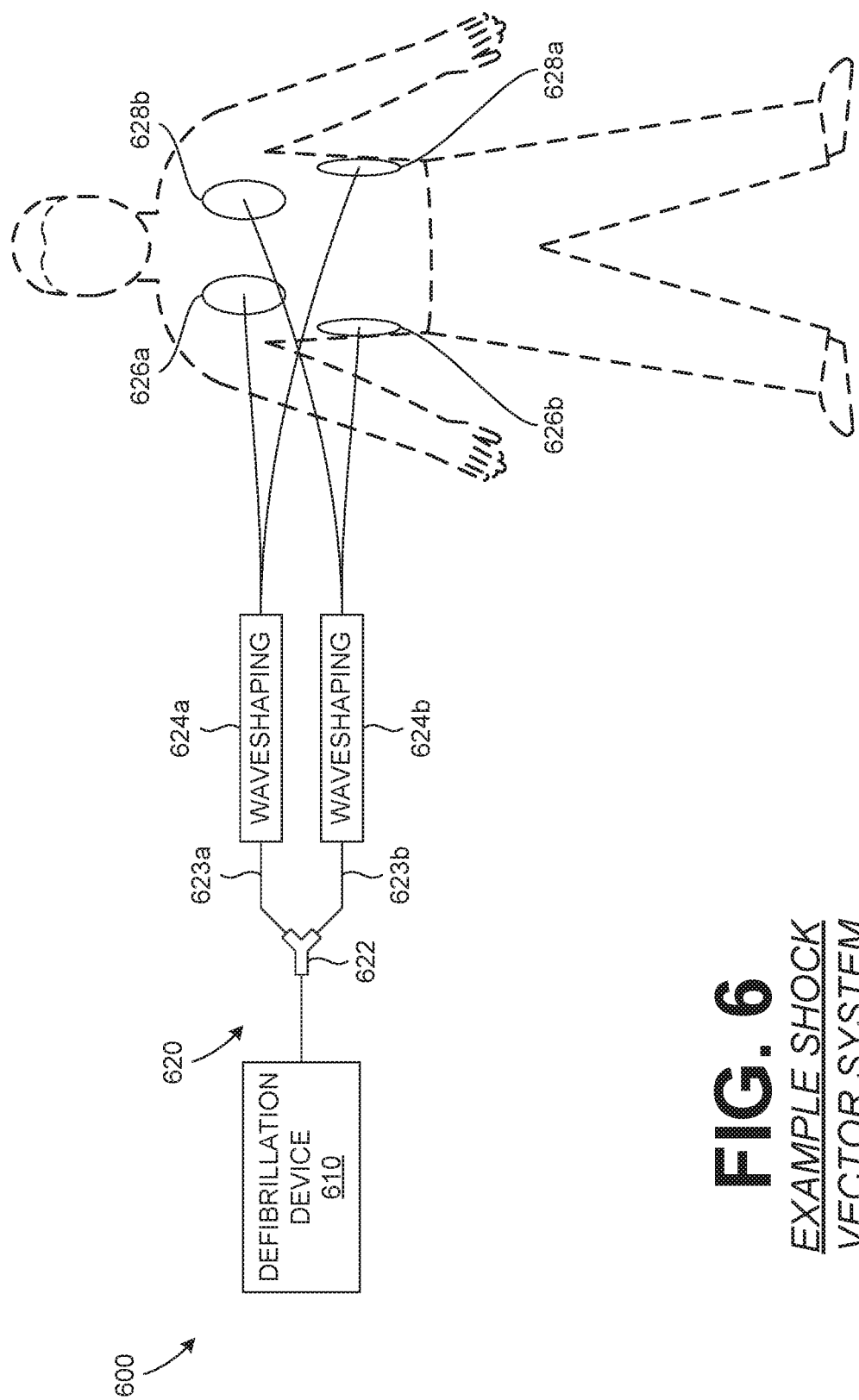
FIG. 6 illustrates an example shock vector system.

An example embodiment of a shock vector system 600 is shown in FIG. 6. A defibrillation device 610 is connected to an electrotherapy cable 620, which can include a "Y-junction" and/or splitter 622 that leads and/or connects to electrotherapy leads 623a, 623b. The electrotherapy leads can include a waveshaping device and/or circuitry 624a, 624b to shape the waveform of an electrotherapy discharge along the electrotherapy leads 623a, 623b. The electrotherapy leads 623a, 623b are connected to electrode pairs 626a, 628a and 626b, 628b. The defibrillation device 610 can output and electrotherapy that can be routed through one or more of the electrode leads 623a, 623b to deliver the electrotherapy along one or more of the vectors between one or more of the electrode pairs 626a, 628a and/or 626b, 628b.

In an example, the defibrillation device 610 can output an electrotherapy as a biphasic waveform, with the first phase of the biphasic waveform being administered through one vector, such as a vector of a first pair of electrodes 626a, 628a, and a second phase of the biphasic waveform being administered through a second vector, such as a vector of a second pair of electrodes 626b, 628b. The splitter 622 and/or the waveshaping circuitry 624a, 624b, can assist with the routing of the first and second phases of the biphasic waveform to the electrode pairs 626a, 628a and 626b, 628b. The phases of the biphasic waveform outputted by the defibrillation device 610 can include various characteristics that can assist with the directing and/or routing of the phases.

The defibrillation device 610 can include hardware and/or software to detect the connection of another electrode pair, such as 626b, 628b, to the electrotherapy cable 620. When the defibrillation device 610 detects the connection of another pair of electrodes, or when otherwise instructed to, the defibrillation device 610 can implement a multi-vector electrotherapy treatment. If another electrode pair is not detected, or if the defibrillation device 610 is otherwise instructed to, the defibrillation device 610 can discharge an electrotherapy over a single electrode pair, such as 626a, 628a. That is, if only a single pair of electrodes is connected to the defibrillation device 610, by default or if the defibrillation device 610 is instructed to, the administration of an electrotherapy will be discharged from the defibrillation device 610 such that it is administered through the single pair of electrodes. If two pairs of electrodes are detected to be connected to the defibrillation device 610, of if the defibrillation device 610 is instructed to, the defibrillation device can administer a multi-vector electrotherapy along the vectors established by each pair of electrodes.

In a further example, the defibrillation device can output a multi-vector electrotherapy as a triphasic waveform. An initial phase, such as a biphasic waveform, can then be administered along a first vector and a second phase, a monophasic waveform, can administered along a second vector. Alternatively, the administration of the biphasic and monophasic waveforms can be reversed in order. Further, the number of vectors, the number of phases of the waveform output by the defibrillation device 610 and/or the number of phases of the waveforms routed through one or more electrode pairs can be increased, modified and/or decreased to achieve a desired and/or necessary total electrotherapy administration.

In another example in which multi-vector electrotherapy is to be administered, the defibrillation device can include hardware and/or software to detect an electrode of a first shock vector is in the proximity of an electrode of the second shock vector and that the two electrodes have opposite polarities. Due to the proximal placement of the two electrodes and their opposite polarities, electrotherapy administered on either shock vector of the two electrodes will tend to flow to the other electrode of opposite polarity rather than through the patient along one or more of the shock vectors. The flow of an electrotherapy from one electrode to another proximal electrode can reduce the efficacy of the administered electrotherapy. In response to detecting the proximal location of the electrodes having opposite polarity, the defibrillation device, such as a 400 of FIG. 4, can reverse the polarity of one of the shock vectors so that the polarity of each of the proximally located electrodes is now substantially the same. The shared polarity of the electrodes will prevent flow of the electrotherapy from one electrode to the other. Alternatively, or in addition, the defibrillation device can alert a user to the proximally located, opposite polarity electrodes to allow the user to reposition the electrodes, to instruct the defibrillation device to alter a polarity of one or more of the electrodes, to alert the user and/or allow the user and/or the defibrillation device to take one or more actions.

Alternative electrode arrangements can be used to achieve similar multi-vector electrotherapy administration as the two or more pairs of electrodes arrangements. In an example 700 shown in FIG. 7, the defibrillation device 710 can be coupled to three electrodes 720a, 720b, 720c that each include a variable resistance 722a, 722b, 722c that can be controlled by the defibrillation device 710. Each of the electrodes 720a, 720b, 720c includes a pad 724a, 724b, 724c that can be placed on and arranged about a patient 702. The defibrillation device 710 can selectively alter the variable resistance 722a, 722b, 722c of each of the electrodes 720a, 720b, 720c to establish a "virtual," or combined shock vector 726 that is formed by the individual shock vectors between one of the electrodes 720a, 720b, 720c and the remaining two electrodes. In the example shown in FIG. 7, a first electrode 720a has a first polarity and a second electrode 720b and a third electrode 720c have a second polarity. In this arrangement an electrotherapy can be administered by the defibrillation device 710, via the first electrode 720a, through the patient 702, towards the second and third electrodes 720b, 720c. By altering the variable resistance of one or more of the second and third electrodes 720b, 720c, the administered electrotherapy can be effectively directed towards one or more of the electrodes 720b, 720c, to generate the combined shock vector 726. In this arrangement 700, the combined, or effective, shock vector 726 can be directed through the patient as desired along a plane formed by the arrangement of the electrodes 720a, 720b, 720c.

Figure 7:
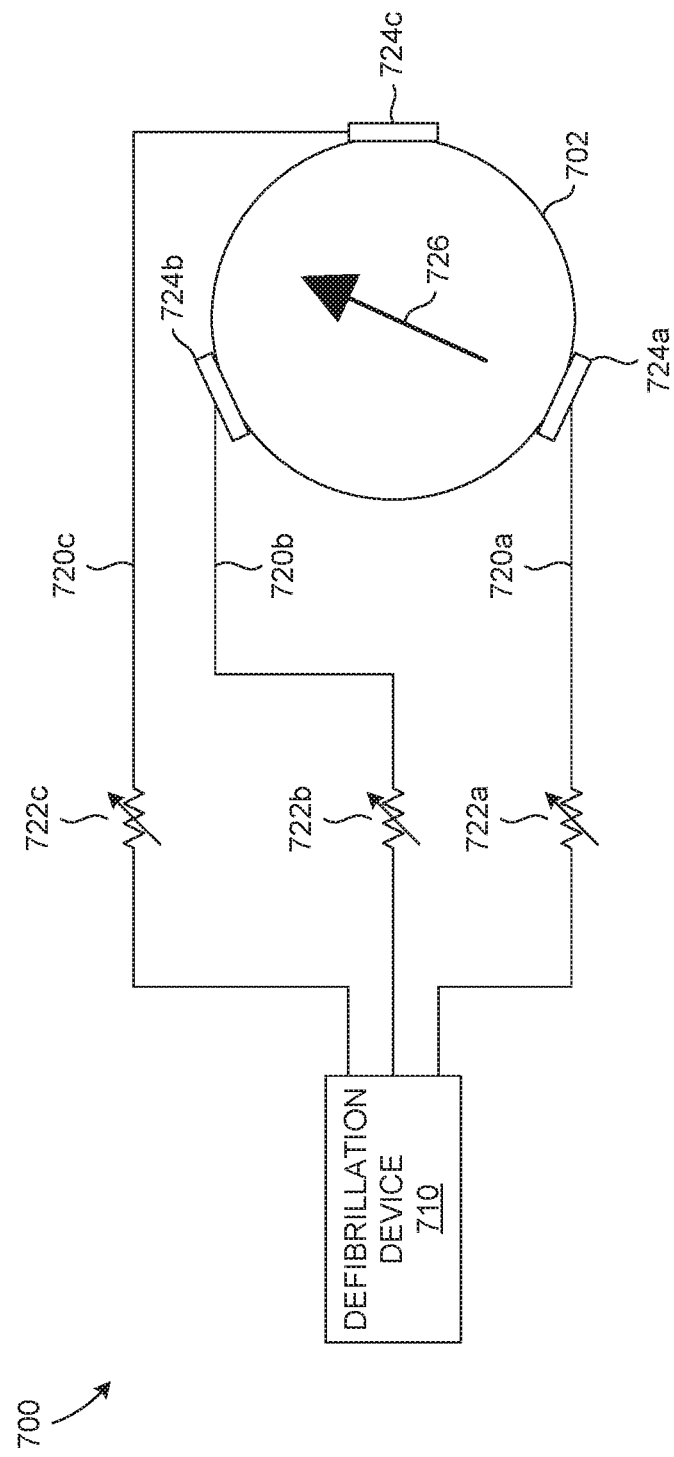
FIG. 7 illustrates an example electrode arrangement on/about a patient.

Additionally, given the arrangement 700 of FIG. 7 and the variable resistance of each electrode 720a, 720b, 720c, the combined shock vector can be redirected during administration of the electrotherapy. That is, as the electrotherapy is being administered by the defibrillation device 710, the variable resistance of one or more of the electrodes 720a, 720b, 720c can be altered to redirect, or reorient, the combined shock vector 726 during a duration of the electrotherapy administration. This can allow the shock vector 726 to be swept through a range of angles during administration of the electrotherapy, which can assist with efficacy of the electrotherapy.

In another example, a defibrillation device, such as 400 of FIG. 4 and/or 710 of FIG. 7, can include hardware and/or software to detect an effectiveness of an electrode pair of two or more electrodes place on and arranged about a patient. That is, the defibrillation device can perform analysis and/or testing to determine the efficacy of a shock vector between an electrode pair of the two or more electrodes affixed to a patient. Using the arrangement 700 of FIG. 7 as a means of an example, the defibrillation device 710 can output small shocks or signals along different vectors formed by the three electrodes 720a, 720b, 720c. The defibrillation device 710, or other device or user, can analyze patient ECG information of each of the small shocks to determine a shock vector, of the tested shock vectors, along which to administer an electrotherapy. The shock vector selected for administration of the electrotherapy can be the shock vector that the ECG data indicated as the most effective shock vector for correcting the abnormal cardiac rhythm. Once a shock vector has been determined, and/or selected, the defibrillation device 710 can administer the electrotherapy along said shock vector.

A defibrillation device, such as 400 of FIG. 4, can include a "boost" function that allows the defibrillation device to deliver an electrotherapy greater, or larger, than would normally be allowed to be administered by the defibrillation device. The boost function could be used to increase the intensity and/or duration of the electrotherapy to assist with correcting an abnormal cardiac rhythm, such as refractory VF. When needed, the "boost" function can be selected to assist with the delivery of an electrotherapy by the defibrillation device. The selection to use the "boost" function can be made automatically by the defibrillation device or can be manually selected by a user, such as when prompted by the defibrillation device that a "boosted" electrotherapy may be warranted. The "boost" function can be selectively used as the increased electrotherapy administration can potentially damage various components and/or systems of the defibrillation device, and/or reduce a safe, usable life of various components and/or systems. The "boost" functionality can be enabled by a secondary device that is coupled to the defibrillation device to assist with administration of an electrotherapy, or can be enabled by one or more components and/or systems of the defibrillation device.

In an example, the "boost" function can be provided by an external device, or booster, that is coupled to the defibrillation device. In an embodiment, the external booster can include one or more capacitors, or energy storage devices, and/or can be placed in-line with the electrotherapy output of the defibrillation device. The external booster can be charged, or energized, by the defibrillation device and its power source, or can include its own power source, such as a batter and/or an external power source that is connected to the external booster. Electrodes for affixing to the patient can be coupled to the external booster so that the electrotherapy is administered by the defibrillation device, "boosted" by the external booster and delivered to the patient via the electrodes. Alternatively, the external booster can be integrated with the electrodes, to form "booster" electrodes, that can be coupled directly to the electrotherapy output of the defibrillation device, substantially similarly to the coupling of non-boosted electrodes to the defibrillation device.

The booster can also be integrated with and/or included in the defibrillation device. In an example, the defibrillation device can include an additional capacitor, or energy storage device, that can be selectively used in the administration of an electrotherapy. The selective use of the integrated booster can be based on a variety of factors, such as the physiological parameters of the patient, other patient data and/or the electrotherapy to be administered. For example, a DSD therapy is determined and/or decided to be administered to correct an abnormal cardiac rhythm of a patient. A boosted electrotherapy can assist with correcting the abnormal cardiac rhythm, so the use of the integrated booster is selected, such as by the defibrillation device and/or a user, and the boosted electrotherapy can be administered.

In another example, the booster device can be modular and selectively coupled to a defibrillation device. The defibrillation device can include an interface, such as an input, for accepting one or more boost modules that can include electrotherapy "boost" functionality, such as a capacitor, or energy storage device. The boost module can be charged by the defibrillation device, by its own power module and/or by an external power source coupled thereto. The boost module can "boost" the electrotherapy administered by the defibrillation device and/or can include an electrotherapy output to which an additional pair of electrodes can be coupled. Coupling a secondary pair of electrodes to the boost module can allow the defibrillation device to administer a DSD, or other electrotherapy, without the use of another defibrillation device. The defibrillation device can charge the boost module, or the boost module can be energized by another source, and can cause an electrotherapy administration by the defibrillation device along a first vector and can then cause the boost module to administer an electrotherapy along a second vector, which can be different than the first vector. In this arrangement, the defibrillation device and the coupled boost module can perform a DSD and/or other multiple shock electrotherapies.

Alternatively, the "boost" functionality can be achieved by over-charging and/or "boosting" an energy storage device, such as a capacitor, of the defibrillation device itself. The capacitor used for electrotherapy administration by the defibrillation device, can be selectively over-charged to discharge a "boosted" electrotherapy. Such over-charging and/or boosting of the defibrillation device's electrotherapy components, modules and/or systems, can reduce the effective life span of the electrotherapy components, thus the selective application of the "boost" functionality. Alternatively, the electrotherapy components, modules and/or systems of the defibrillation device can have increased capacity to allow for the "boosted" functionality without reducing the effective life span of the electrotherapy components, modules and/or systems. Further, to assist with preventing damage to the electrotherapy components, modules and/or systems, a thermoregulation module, such as 440, of the defibrillation device can cool the electrotherapy components, modules and/or systems when a "boosted" electrotherapy is to be administered. The cooling of the electrotherapy components, modules and/or systems can prevent thermal stress in the electrotherapy components, modules and/or systems that could cause electrotherapy components, modules and/or systems failure and/or reduced usable life.

To assist with charging, or energizing, the "boost" functionality, devices, modules and/or systems of the defibrillation device, the defibrillation and/or "boost" device can include reenergizing circuitry, devices and/or systems to assist with reenergizing the "boost" device during administration of an electrotherapy. The reenergizing circuitry can assist with reenergizing not only the "boost" device, but also reenergizing the defibrillation device therapy module. The ability to rapidly reenergize the "boost" and/or defibrillation device can reduce the delay between the delivery of subsequent electrotherapy administrations, which can assist with treatment of a patient's abnormal cardiac rhythm.

In a further example, the defibrillation device can administer a train of pacing stimuli in conjunction with the administration of an electrotherapy. The pacing stimuli can be various pacing stimuli, such as anti-tachycardia pacing stimuli, to assist with correcting an abnormal cardiac rhythm. Additionally, the train of pacing stimuli can assist with the efficacy of the electrotherapy.

To assist with reducing the duration between subsequent electrotherapy administrations, a defibrillation device can include hardware and/or software to allow a therapy module, such as 460, and/or one or more energy storage devices therein, to be energized while an electrotherapy is administered. Energizing an electrotherapy capacitor of the defibrillation device during administration of an electrotherapy can reduce the duration required to charge the electrotherapy capacitor to a desired level for a subsequent electrotherapy administration. Correction of abnormal cardiac rhythms is time sensitive and the reduction in the delay between subsequent electrotherapy administrations can increase the number of electrotherapies that can be administered during the critical treatment period.

As previously discussed, a defibrillation device, such as 400 of FIG. 4, can include hardware and/or software to allow for the recording of various data regarding the defibrillation device, its use and maintenance, and/or other data the defibrillation device collects, accesses and/or uses. In an example, the defibrillation device can generate a record of each use of the defibrillation device in a treatment of a patient. The defibrillation device can automatically generate this record or a user or other, such as an external system or device, can cause the record to be generated. As an example, the use of a defibrillator in a DSD procedure can cause the defibrillator to record an event indicating the use of the defibrillator in a DSD procedure. The defibrillation device can store recent data as general data and when a record generation is initiated, the defibrillation device can store at least a portion, or none, of the recent data as part of the record being generated. This can allow the defibrillation device to be used and a record to be generated after the use of the device is completed. Additionally, this functionality can allow the record to be generated during use of the device. For example, a user can begin using the defibrillation device to treat a patient and a record generation can be initiated during the treatment. The generated record can include data relating to the treatment prior to the initiation of the record generation and can continue to collect and record data as the treatment progresses until the treatment is complete and the record can be finalized. Various events and/or uses can cause the defibrillation device to automatically generate, or initiate the generation of, a record of the event.

In a DSD use, the record can be initiated by a detection of an electrotherapy administration by another defibrillation device. Patient physiological parameters and/or data, such as ECG data, can indicate that an electrotherapy was administered to the patient and the defibrillation device can generate or initiate the generation of a record of the DSD treatment. This detection capability does not require that the defibrillation device be communicatively coupled to another defibrillation device to begin collecting a record of the DSD treatment event.

The recording of an event by the defibrillation device can be documented, received and/or stored by a secondary device and/or systems, such as an electronic patient care reporting (ePCR) or care-processing application or system which the defibrillation device is in communication with.

Various recording data, such as an event type (i.e. administration of a DSD electrotherapy), can cause at least a portion of the record, and/or an indication of the event, to be transmitted to a remote device and/or system, such as a remote stakeholder. Example remote stakeholders can include a medical director, personnel at a hospital that is to receive the patient, a research coordinator and/or other persons/systems. The remote stakeholders who receive the record/indication from the defibrillation device can be determined by characteristics of the record/indication, such as the event type. In the case of a record/indication of a DSD therapy administration, the remote stakeholder can receive the record/indication to be informed that the patient undergoing treatment is "difficult-to-defibrillate." This consideration can allow the remote stakeholder, such as a treating physician, to make treatment decisions based on the "difficult-to-defibrillate" status of the patient. Additionally, the record/indication could cause the record/indication to be received by other remote stakeholders, such as additional treatment services and/or specialties, to inform them of the possibility and/or likelihood of receiving the patient for treatment. For example, for the record/indication of the "difficult-to-defibrillate" patient, additional remote stakeholder related to cardiac specialties of a hospital, such as a cath lab and/or other departments/personnel, can receive the record/indication to allow them to prepare for treatment of the patient upon their arrival to the hospital. Various other data related to the patient, such as physiological data and/or other patient data, can be included in the record/indication to provide additional information to the treating personnel/departments for their preparation to treat the patient.

Additionally, the record/indication can be tracked by the defibrillation device and/or a remote device/system to analyze the preceding patient treatment and provide recommendations for subsequent treatment. For example, if the record/indication indicates the unsuccessful application of one or more electrotherapies, such as a DSD therapy, a protocol of the defibrillation device and/or remote device/system can recommend an alternative treatment or therapy strategy. Alternative treatment/therapy strategies can include the application of mechanical chest compressions, transport of the patient to a various cardiac specialty personnel/departments and/or other recommendations. Additionally, this recommendation process can include an intervening review process in which the recommended alternative therapies/strategies are forwarded to a remote system, device and/or user for review and/or approval. In an embodiment, the recommended alternative therapies/strategies may not be provided to the user before the review and approval of the recommendations. Alternatively, the recommendations can be provided prior to their review and the review process can determine the recommendations are correct and provide no intervention, or can determine the recommendations require modification and/or replacement and can provide the necessary intervention to provide the updated, or new, recommendations.

In treatments in which multiple defibrillation devices are used, the treatment event records from each of the defibrillation devices can be collected and/or merged in a single record that can be stored in a remote system/device and/or in one or more of the defibrillation devices used. The event records can include various information and/or data related to the treatment by, or use of, the defibrillation device. Example data can include recorded ECG waveforms, events, patient information, logs of electrotherapy administrations, various maintenance records and/or other data/information. The event records from each defibrillation device can be transmitted to a remote system/device and merged, such as by using the time stamps and/or other data contained within each record. This merging synchronizes the two records so that the various actions and/or uses of each defibrillation device can be reviewed chronologically together. The merged record can then be transmitted to and/or stored by one or more of the defibrillation devices and/or can be stored in a remote system/device.

The merged data can be used to create an incident report related to the treatment. The incident report can be a general report or can be specific to the treatment, such as the electrotherapy administered. The incident report can be generated in real-time during the event or can be compiled after the event is complete. Further, one or more of the defibrillation devices and/or an external device, such as a device connected to a local network established by the defibrillation devices, can display the incident report. Additionally, the incident report can be transmitted to a remote system/device for review, such as a post-event-review program. This can allow the event to be reviewed for various purposes, such as teaching and/or critique of the treatment performed. The incident report can include various information regarding the treatment, including data regarding the administration of an electrotherapy(s), patient information and/or other information related to the treatment and/or event. An example incident report can include a "DSD incident report," that can be created by incorporating data from one or both defibrillators used in a DSD procedure. The "DSD incident report" can include elements such as the number of single and DSD shocks administered and/or ECG snapshots of the pre-shock and post-shock rhythms surrounding each shock.

It will be appreciated that variants of the above-disclosed and other features and functions, or alternatives thereof, may be combined into many other different devices, systems and/or applications. Other embodiments Various presently unforeseen or unanticipated alternatives, modifications, variations, or improvements therein may be subsequently made by those skilled in the art which are also intended to be encompassed by the following claims.

The invention claimed is:
1. A defibrillation device, comprising:
a defibrillation therapy module configured to discharge one or more energies;
a physiological parameter module configured to receive one or more physiological parameters, including at least electrocardiogram (ECG) data; and
a control module configured to:
analyze the one or more physiological parameters to determine an indication for an electrotherapy administration;
receive a review of the ECG data; and
generate an indication for an electrotherapy treatment that includes a dual-sequential defibrillation electrotherapy configured to be delivered by a combination of the defibrillation device and another defibrillation device, the electrotherapy treatment based at least in part on one or any combination of the one or more physiological parameters, the indication for the electrotherapy administration, the review of the ECG data, and user input.

2. The defibrillation device of claim 1, wherein the physiological parameter module or the control module is further configured to output the ECG data to a display.

3. The defibrillation device of claim 1, wherein the control module is further configured to filter the ECG data to substantially remove cardiopulmonary resuscitation (CPR) artifacts prior to the review of the ECG data.

4. The defibrillation device of claim 1, wherein the indication for the electrotherapy administration includes an indication of electrotherapy administration for refractory ventricular fibrillation.

5. The defibrillation device of claim 1, wherein the review of the ECG data includes an indication of refractory ventricular fibrillation.

6. The defibrillation device of claim 1, wherein the determination of the dual-sequential defibrillation electrotherapy is further based at least in part on an indication of refractory ventricular fibrillation.

7. The defibrillation device of claim 1, wherein the control module is further configured to receive the review of the ECG data from the defibrillation device or the another defibrillation device.

8. The defibrillation device of claim 1, wherein the control module is further configured to review the ECG data and apply a review analysis of the ECG data for the determination of the dual-sequential defibrillation electrotherapy.

9. The defibrillation device of claim 1, further comprising a user interface configured to receive input from a rescuer related to the review of the ECG data.

10. The defibrillation device of claim 1, wherein the defibrillation device is a manual defibrillator, a monitor-defibrillator, or an automated external defibrillator (AED).

11. The defibrillation device of claim 1, wherein the control module is further configured to automatically generate the instructions for the electrotherapy treatment.

12. The defibrillation device of claim 1, wherein the control module is further configured to generate a user output that includes the indication for electrotherapy treatment.

13. The defibrillation device of claim 12, wherein the user output includes a rescuer prompt to initiate the dual-sequential defibrillation electrotherapy.

14. The defibrillation device of claim 1, wherein the control module is further configured to identify an outcome of one or more previously administered electrotherapies.

15. The defibrillation device of claim 14, wherein the outcome of the one or more previously administered electrotherapies includes an analysis of whether the one or more previously administered electrotherapies terminated ventricular fibrillation.

16. The defibrillation device of claim 14, wherein the outcome of the one or more previously administered electrotherapies includes a tally of the success of each previously administered electrotherapy.

17. The defibrillation device of claim 16, wherein the tally includes a determination of whether each of the previously administered electrotherapies terminated ventricular fibrillation.

18. The defibrillation device of claim 14, wherein the control module is further configured to generate the instructions for the indication of the electrotherapy treatment that includes the dual-sequential defibrillation electrotherapy based at least in part on the outcome of the one or more previously administered electrotherapies.

19. A defibrillation system, comprising:
a first defibrillation device, including a first defibrillation therapy module configured to output a first energy;
a second defibrillation device, including a second defibrillation therapy module configured to output a second energy; and
a control module configured to:
receive one or more physiological parameters, including at least electrocardiogram (ECG) data;
analyze the one or more physiological parameters to determine an indication for an electrotherapy administration;
receive a review of ECG data; and
generate an indication for a dual-sequential defibrillation electrotherapy based at least in part on one or any combination of the one or more physiological parameters, the indication for the electrotherapy administration, the review of the ECG data, and user input.

20. The defibrillation system of claim 19, wherein the first defibrillation device and the second defibrillation device are each selected from one of a defibrillator, a monitor-defibrillator and an automated external defibrillator (AED).

21. The defibrillation system of claim 19, wherein the control module is included in the first defibrillation device and, the control module is further configured to control the output of the second energy by the second defibrillation device.

22. The defibrillation system of claim 19, wherein control module is further configured to determine the dual-sequential defibrillation electrotherapy based at least in part on an indication of refractory ventricular fibrillation.

23. The defibrillation system of claim 19, wherein the dual-sequential defibrillation electrotherapy includes at least a first characteristic of the first energy, a second characteristic of the second energy and a timing relationship.

24. The defibrillation system of claim 23, wherein the timing relationship includes temporal data regarding the delivery of the second energy relative to the delivery of the first energy.

25. The defibrillation system of claim 19, wherein the dual-sequential defibrillation electrotherapy includes an ordered administration of the first energy and the second energy based on the first defibrillation device type and the second defibrillation device type.

26. The defibrillation system of claim 19, wherein one or both of the first defibrillation device and the second defibrillation device is configured to operate in a dual-sequential defibrillation operating mode.

27. The defibrillation system of claim 26, wherein the first defibrillation device is configured to operate in the dual-sequential defibrillation operating mode based on a determination that the second defibrillation device is coupled to a patient to which the first defibrillation device is also coupled.

* * * * *